United States Patent
Bienewald et al.

(10) Patent No.: US 7,723,521 B2
(45) Date of Patent: May 25, 2010

(54) AZAPERYLENES AS ORGANIC SEMICONDUCTORS

(75) Inventors: Frank Bienewald, Hegenheim (FR); Beat Schmidhalter, Bubendorf (CH); Ulrich Berens, Binzen (DE); Hans Jürg Kirner, Pratteln (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 203 days.

(21) Appl. No.: 11/919,605

(22) PCT Filed: May 3, 2006

(86) PCT No.: PCT/EP2006/062007
§ 371 (c)(1),
(2), (4) Date: Oct. 30, 2007

(87) PCT Pub. No.: WO2006/120143
PCT Pub. Date: Nov. 16, 2006

(65) Prior Publication Data
US 2009/0101890 A1    Apr. 23, 2009

(30) Foreign Application Priority Data
May 13, 2005    (EP)    ................. 05104009

(51) Int. Cl.
*C07D 471/02*    (2006.01)
*H01L 21/02*    (2006.01)

(52) U.S. Cl. ............. 546/28; 438/46; 438/99; 546/49; 428/930

(58) Field of Classification Search ............ 546/28, 546/49; 437/1; 428/930; 438/46, 99
See application file for complete search history.

(56) References Cited

U.S. PATENT DOCUMENTS

| | | | |
|---|---|---|---|
| 5,028,643 A | 7/1991 | Jaffe | 524/90 |
| 6,252,245 B1 | 6/2001 | Katz et al. | 257/40 |
| 6,690,029 B1 | 2/2004 | Anthony et al. | 257/40 |
| 2002/0164835 A1 | 11/2002 | Dimitrakopoulos et al. | 438/99 |
| 2003/0105365 A1 | 6/2003 | Smith et al. | 568/774 |
| 2003/0144562 A1 | 7/2003 | Afzali-Ardakani et al. | 570/212 |
| 2004/0076853 A1 | 4/2004 | Jarikov | 428/690 |
| 2004/0116700 A1 | 6/2004 | Hartmann et al. | 546/13 |

FOREIGN PATENT DOCUMENTS

WO    02/068431    9/2002

OTHER PUBLICATIONS

Johansson, L. et al.: Photophysics, molecular reorientation in solution and X-Ray structure of a new fluorescent probe, 1,7-diazaperylene. J. Chem. Soc. Faraday Trans. vol. 89, pp. 49-54, 1993.*
J. Mizuguchi, Dyes and Pigments, vol. 35, No. 4, pp. 347-360, (1997).
Patent Abstracts of Japan Publication No. 2000231987, Aug. 22, 2000.
K. Kitahara et al., J. Heterocyclic Chem., vol. 25, pp. 1063-1065, (1988).
Patent Abstracts of Japan Publication No. 63-193960, Aug. 11, 1988.
Horowitz, Advanced Materials 10, 365 (1998).

* cited by examiner

*Primary Examiner*—Charanjit S Aulakh
(74) *Attorney, Agent, or Firm*—Shiela A. Loggins (57) ABSTRACT

A novel semiconductor device comprises an azaperylene organic semiconductor of the formula I

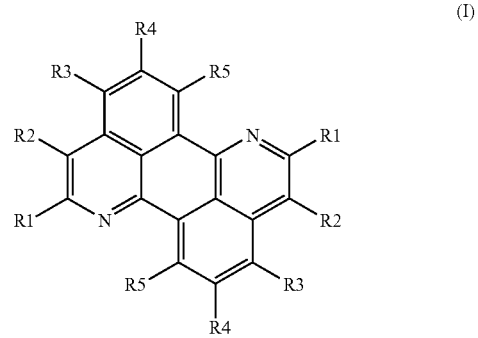

wherein the substitutents are defined herein.

19 Claims, 2 Drawing Sheets

Fig. 1: Emission and excitations spectrum compound No. 653

AZAPERYLENES AS ORGANIC SEMICONDUCTORS

The present application pertains to a semiconductor device comprising an azaperylene as organic semiconductor, to a process for the preparation of said devices, to novel azaperylenes useful inter alia in said process, as well as to the use of an azaperylene, or a precursor thereof, as an organic semiconductor for the preparation of an electronic device.

Organic semiconductor devices, e.g. organic field effect transistors (OFETs), promise a number of advantages over traditional inorganic semiconductors, such as low-cost manufacturing or compatibility with flexible substrates. Besides certain polymers, a number of condensed aromatic compounds such as pentacene have been found to exhibit useful semiconducting properties, inter alia characterized by high charge carrier (field effect) mobility, high on/off current ratio, low sub-threshold voltage. These advantageous features are, however, often compromised by factors like the necessity to use vapour deposition for the preparation of thin film devices, or lack of stability due to effects like recrystallization, phase transition or environmental influences.

Ideally, an organic semiconductor should be soluble in organic solvents to be suitable for application on large areas by inexpensive methods, such as, stamping, screen printing and spin-coating.

In order to improve the properties of organic semiconductors, structural modifications have been introduced into condensed aromatics, mainly in order to improve the solubility of these compounds; examples are Diels-Alder adducts which may be thermally reconverted into pentacene (US-2003-0144526), substituted pentacenes (US-2003-0105365, U.S. Pat. No. 6,690,029), tetracarboxylic acid diimides of naphthalene (U.S. Pat. No. 6,252,245) or perylene (US-2002-0164835).

There is a need for organic semiconductors that can provide stable, reproducible electronic performance characteristics and that exhibit good charge-carrier mobilities while allowing for low-cost manufacturing or providing the possibility for solvent processing.

Certain tetrabenzo-diazaperylenes have been proposed for use as pigments for the coloration of organic materials (see U.S. Pat. No. 5,028,643; JP-A-63-193960). K. Kitahara, H. Nishi, J. Heterocycl. Chem. 1988, 25, 1063, describe the conversion of 1,8-diaza-2,9-diethoxycarbonyl-3,10-diphenyl-2,9-dihydro-pentacene into a diazaperylene.

WO 02/068431 discloses the preparation of soluble boron complexes of certain diazaperylenes, which are reported as being useful for the preparation of organic light emitting diodes (OLEDs). Use of 1,7-diazaperylene for the same purpose is recommended in JP-A-2000-231987.

It has now been found that certain substituted diazaperylenes have good semiconducting properties and thus may be used as organic semiconductors in corresponding devices not only as diodes or OLEDs but especially as organic field effect transistors (OFETs), which are advantageously prepared as thin film transistors (OTFTs).

The subject of the invention therefore generally pertains to a semiconductor device comprising an azaperylene organic semiconductor of the formula I wherein each of R1, R2, R3 and R4 are H, unsubstituted or substituted alkyl, unsubstituted or substituted alkenyl, unsubstituted or substituted alkynyl, unsubstituted or substituted aryl, halogen, Si(R11)$_3$, XR6; or one or more of R1 and R2, R2 and R3, R3 and R4, together with the carbon atoms they are bonding to, form a saturated or unsaturated, unsubstituted or substituted carbocyclic or heterocyclic ring;

R5 is OR7, SR7, NR7R8, unsubstituted or substituted alkyl, unsubstituted or substituted alkenyl, unsubstituted or substituted alkynyl, or unsubstituted or substituted aryl;

R6 is Si(R11)$_3$, unsubstituted or substituted alkyl, unsubstituted or substituted alkenyl, unsubstituted or substituted alkynyl, unsubstituted or substituted aryl;

R7 is H, unsubstituted or substituted alkyl, unsubstituted or substituted alkenyl, unsubstituted or substituted alkynyl, unsubstituted or substituted aryl;

X is O, S, NR8;

R8 is H, unsubstituted or substituted alkyl, unsubstituted or substituted alkenyl, unsubstituted or substituted alkynyl, unsubstituted or substituted aryl.

Alkyl stands for any acyclic saturated monovalent hydrocarbyl group; alkenyl denotes such a group but containing at least one carbon-carbon double bond (such as in allyl); similarly, alkynyl denotes such a group but containing at least one carbon-carbon triple bond (such as in propargyl). In case that an alkenyl or alkynyl group contains more than one double bond, these bonds usually are not cumulated, but may be arranged in an alternating order, such as in —[CH═CH—]$_n$ or —[CH═C(CH$_3$)—]$_n$, where n may be, for example, from the range 2-50. Preferred alkyl contains 1-22 carbon atoms; preferred alkenyl and alkinyl each contains 2-22 carbon atoms, especially 3-22 carbon atoms.

Any alkyl moiety of more than one, especially more than 2 carbon atoms, or such alkyl or alkylene moieties which are part of another moiety, may be interrupted by a heterofunction such as O, S, COO, OCNR10, OCOO, OCONR10, NR10CNR10, or NR10, where R10 is H, $C_1$-$C_{12}$alkyl, $C_4$-$C_{12}$cycloalkyl. They can be interrupted by one or more of these spacer groups, one group in each case being inserted, in general, into one carbon-carbon bond, with hetero-hetero bonds, for example O—O, S—S, NH—NH, etc., not occurring; if the interrupted alkyl is additionally substituted, the substituents are generally not α to the heteroatom. If two or more interrupting groups of the type —O—, —NR10-, —S— occur in one radical, they often are identical.

The term alkyl, wherever used, thus mainly embraces especially uninterrupted and, where appropriate, substituted $C_1$-$C_{22}$alkyl such as methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl. Alkoxy is alkyl-O—; alkylthio is alkyl-S—.

The term aryl, wherever used, mainly embraces $C_1$-$C_{18}$aromatic moieties, which may be heterocyclic rings containing, as part of the ring structure, one or more heteroatoms mainly selected from O, N and S; hydrocarbon aryl examples mainly are $C_6$-$C_{18}$ including phenyl, naphthyl, anthrachinyl, anthracenyl, fluorenyl; examples for heterocyclics ($C_1$-$C_{18}$) include those of the following table:

| ring structure | name | monovalent residue |
|---|---|---|
|  | pyridine | pyridyl |
|  | pyrimidine | pyrimidyl |
|  | pyridazine | pyridazyl |
|  | pyrazine | pyrazyl |
|  | purine | purinyl |
|  | pteridine | pteridyl |

-continued

| ring structure | name | monovalent residue |
|---|---|---|
|  | thiophene | thiophenyl |
|  | benzothiophene | benzothiophenyl |
|  | pyrrol | pyrryl |
|  | furane | furyl |
|  | benzofurane | benzofuryl, |
|  | indole | indyl |
|  | carbazole | carbazolyl |
|  | benzotriazole | benzotriazolyl |
|  | tetrazole | tetrazolyl |
|  | thiazole | thiazolyl |
|  |  | thienothienyl |
|  |  | dithiaindacenyl |
|  |  | chinolyl |

-continued

| ring structure | name | monovalent residue |
|---|---|---|
|  | | isochinolyl |
|  | | chinoxalyl |
|  | | acridyl | as well as azanaphthyl, phenanthrolyl, triazinyl, tetrahydronaphthyl, thienyl, pyrazolyl, imidazolyl, most preferred is phenyl, thiophenyl.

Where residues are substituted, substituents usually bond to a carbon atom and are selected from $C_1$-$C_{22}$alkoxy, $C_1$-$C_{22}$alkyl, $C_4$-$C_{12}$cycloalkoxy, $C_4$-$C_{12}$cycloalkyl, OH, halogen, aryl such as phenyl and naphthyl; saturated carbons also may be substituted by oxo (=O); adjacent substituents may be linked together, e.g. to form a lactone, anhydride or imide ring. Preferred substituents are alkyl or alkoxy; of specific technical interest are those containing 4 or more, especially 5 or more carbon atoms (see below).

Halogen denotes 1, Br, Cl, F, preferably Cl, F, especially F. Also of specific technical interest are perhalogenated residues such as perfluoroalkyl, e.g. of 1 to 12 carbon atoms such as $CF_3$.

Substituted silyl is preferably Si substituted by two or preferably three moieties selected from unsubstituted or substituted hydrocarbyl or hydrocarbyloxy (wherein the substituents are preferably other than substituted silyl), as defined above, or by unsubstituted or substituted heteroaryl. In case that Si carries only two substituents, the silyl group is of the type —SiH($R_2$) with R preferably being hydrocarbyl. More preferred are three $C_1$-$C_{20}$-alkyl or -alkoxy substituents, i.e. substituted silyl then is Si($R11$)$_3$ with R11 being $C_1$-$C_{20}$-alkyl or -alkoxy, especially three $C_1$-$C_8$-alkyl substitutents, such as methyl, ethyl, isopropyl, t-butyl or isobutyl, or methoxy, ethoxy, propoxy.

Preferred compounds of the formula I are those wherein each of the adjacent residues R1 and R2, R3 and R4, together with the carbon atoms they are bonding to, form a saturated or unsaturated, unsubstituted or substituted carbocyclic or heterocyclic ring; especially preferred are unsubstituted or substituted 5- or 6-membered carbocyclic or N- or S-heterocyclic rings. Examples for such rings embraced by compounds of the formula I in annellated form are of the type benzene, pyridine, tri- or tetrahydrobenzene ("cyclohexane"), furan, dihydrofuran, thiophene, dihydrothiophene, pyrrole, dihydropyrrole, cyclopentene; most important are 6-membered carbocyclic aromatic rings (benzene rings) and 5-membered N- and/or S-heterocyclic aromatic rings.

R5 is preferably selected from OR7, SR7; and in cases where another substituent of 4 or more carbon atoms is present, also may be hydrogen;

R7 is preferably selected from H, unsubstituted or substituted alkyl or alkenyl, unsubstituted or substituted aryl.

More preferred compounds of the formula I are those wherein each of the adjacent residues R1 and R2, R3 and R4, together with the carbon atoms they are bonding to, form a saturated or unsaturated carbocyclic 6-membered ring or N- and/or S-heterocyclic 5-membered ring;

R5 is OR7, SR7; and

R7 is H, unsubstituted or substituted alkyl.

Examples of such compounds conform to the structure II wherein

A1, A2, A3 and A4 each independently are bridge members completing, together with the carbon atoms they are bonding to, an unsubstituted or substituted aromatic carbocyclic 6-membered ring or N- and/or S-heterocyclic 5-membered ring, R7 independently is H or unsubstituted or substituted alkyl, unsubstituted or substituted alkenyl, unsubstituted or substituted alkynyl, unsubstituted or substituted aryl, and

X is O, S, NR8;

R8 is H, $C_1$-$C_{12}$alkyl or $C_3$-$C_{12}$alkenyl which is unsubstituted or substituted by halogen or OH or NR10R10, where R10 is H, $C_1$-$C_{12}$alkyl, $C_4$-$C_{12}$cycloalkyl.

In preferred compounds of the formula II, R7 is as defined above for preferred compounds of the formula I; X is most preferably O.

Most preferred examples of compounds of the formula I conform to the structure III (III)

wherein

R independently is H, halogen, OH, unsubstituted or substituted alkyl, unsubstituted or substituted alkoxy, unsubstituted or substituted alkylthio, unsubstituted or substituted aryl, and R7 independently is H, alkyl, alkenyl or alkynyl, especially alkyl.

Compounds of formula I of specific technical interest contain R5 as OR7 or SR7, where R7 is H, unsubstituted or substituted alkyl, unsubstituted or substituted Aryl; and/or wherein at least one of R1-R5, especially 2 thereof such as R2 or R7, contain an alkyl or alkylene chain of 4 or more, especially 5 or more carbon atoms. Examples of such compounds are those of the above formula (III), wherein at least one of R and $R_7$, especially both residues R and/or both residues $R_7$, contain an alkyl or alkylene chain of 4 or more, especially 5 or more carbon atoms; examples for such residues are $C_4$-$C_{22}$alkyl, $C_{10}$-$C_{22}$phenylalkyl, or such residues interrupted in the aliphatic part by O, S, NR10, COO, OCNR10, OCOO, OCONR10, NR10CNR10, especially O.

Thus, the invention further pertains to a novel compound of the formula I as described above, wherein at least one of R1, R2, R3, R4, R6, R7 is $C_4$-$C_{22}$alkyl, $C_{10}$-$C_{22}$phenylalkyl, or such residues interrupted by O, S, NR10, COO, OCNR10, OCOO, OCONR10, NR10CNR10; preferably to a compound of the formula III, (III)

wherein each R independently is selected from H, halogen, OH, unsubstituted or substituted alkyl, unsubstituted or substituted alkoxy, unsubstituted or substituted alkylthio, unsubstituted or substituted aryl;

each R7 independently is selected from H, alkyl, alkenyl or alkynyl, especially alkyl, and at least one of R, $R_7$ is $C_4$-$C_{22}$alkyl, $C_{10}$-$C_{22}$phenylalkyl, or $C_4$-$C_{22}$alkyl, $C_{10}$-$C_{22}$phenylalkyl interrupted in the aliphatic part by O, S, NR10, COO, OCNR10, OCOO, OCONR10, NR10CNR10.

Preferred compounds of the invention are more soluble than pentacene or perylene in organic solvents and are therefore better candidates for economical solution processing methods of deposition.

The novel compounds of the invention are also useful as fluorescent dyes or as infrared absorbing materials.

Preparation

In general, compounds of the formula I may be obtained according to, or in analogy to, methods described by K. Kitahara, H. Nishi, J. Heterocycl. Chem. 1988, 25, 1063

Preferred compounds of the formula I may be obtained conveniently by heating of a precursor of the formula II'

(II')

wherein

R1, R2, R3 and R4 and X are as defined for formula I, especially wherein X is O, and R' is H, unsubstituted or substituted alkyl, unsubstituted or substituted aryl.

Heating is usually to about 60-500° C., preferably to about 100-350° C., especially to about 60-200° C. In the most preferred process, where a thin film of the precursor of formula II' is applied to the substrate as a latent semiconductor, the transfer is achieved at a temperature up to 150° C.

Compounds of the formula I may also be obtained according or in analogy to methods described in DE-A-4005056.

For example, preparation of a preferred compound of the formula I may be conveniently be effected according to the scheme:

by application of heat; R' and R are as defined above.

Compounds of the formula I as well as preferred compounds of formulae II or III wherein R7 is H may be conveniently transferred into the desired derivatives wherein R7 is an organic residue as defined above by methods of etherification, thioetherification or amination known in the art.

The precursor of formula II usually is well soluble and may be thus be applied to a substrate by conventional techniques such as dipping, printing, stamping etc., especially as a thin film.

The semiconducting layer of compounds of the formula I may be prepared by heating of a previously prepared layer of the precursor of the formula II (latent semiconductor).

Therefore, it is an object of the present invention to prepare thin films of an azaperylene by solid state conversion of thin films of an the organic solvent soluble precursor of formula II to the azaperylene. It is further another object of the present invention to provide films of an azaperylene for the fabrication of TFT devices that are prepared by a low to moderate temperature conversion of a precursor thereof to the azaperylene compound at about 60° C. to about 300° C.

It is another object of the present invention to prepare thin films of an organic solvent soluble precursor of formula II by applying a solution of the precursor in an organic solvent onto a substrate and thereafter removing the solvent.

It is yet another object of the present invention to use a thin film of an azaperylene compound in a thin film transistor in which the azaperylene compound film acts as a p-type or n-type semiconductor channel.

Semiconductor Devices

The compounds of the invention can be used as the semiconductor layer in semiconductor devices. There are numerous types of semiconductor devices. Common to all is the presence of one or more semiconductor materials. Semiconductor devices have been described, for example, by S. M. Sze in Physics of Semiconductor Devices, 2.sup.nd edition, John Wiley and Sons, New York (1981). Such devices include rectifiers, transistors (of which there are many types, including p-n-p, n-p-n, and thin-film transistors), light emitting semiconductor devices (for example, organic light emitting diodes), photoconductors, current limiters, thermistors, p-n junctions, field-effect diodes, Schottky diodes, and so forth. In each semiconductor device, the semiconductor material is combined with one or more metals or insulators to form the device. Semiconductor devices can be prepared or manufactured by known methods such as, for example, those described by Peter Van Zant in Microchip Fabrication, Fourth Edition, McGraw-Hill, New York (2000).

A particularly useful type of transistor device, the thin-film transistor (TFT), generally includes a gate electrode, a gate dielectric on the gate electrode, a source electrode and a drain electrode adjacent to the gate dielectric, and a semiconductor layer adjacent to the gate dielectric and adjacent to the source and drain electrodes (see, for example, S. M. Sze, Physics of Semiconductor Devices, 2.sup.nd edition, John Wiley and Sons, page 492, New York (1981)). These components can be assembled in a variety of configurations. More specifically, an organic thin-film transistor (OTFT) has an organic semiconductor layer.

Typically, a substrate supports the OTFT during manufacturing, testing, and/or use. Optionally, the substrate can provide an electrical function for the OTFT. Useful substrate materials include organic and inorganic materials. For example, the substrate can comprise inorganic glasses, ceramic foils, polymeric materials (for example, acrylics, epoxies, polyamides, polycarbonates, polyimides, polyketones, poly(oxy-1,4-phenyleneoxy-1,4-phenylenecarbonyl-1,4-phenylene) (sometimes referred to as poly(ether ether ketone) or PEEK), polynorbornenes, polyphenyleneoxides, poly(ethylene naphthalenedicarboxylate) (PEN), poly(ethylene terephthalate) (PET), poly(phenylene sulfide) (PPS)), filled polymeric materials (for example, fiber-reinforced plastics (FRP)), and coated metallic foils.

The gate electrode can be any useful conductive material. For example, the gate electrode can comprise doped silicon, or a metal, such as aluminum, chromium, gold, silver, nickel, palladium, platinum, tantalum, and titanium. Conductive polymers also can be used, for example polyaniline or poly (3,4-ethylenedioxythiophene)/poly(styrene sulfonate) (PEDOT:PSS). In addition, alloys, combinations, and multilayers of these materials can be useful. In some OTFTs, the same material can provide the gate electrode function and also provide the support function of the substrate. For example, doped silicon can function as the gate electrode and support the OTFT.

The gate dielectric is generally provided on the gate electrode. This gate dielectric electrically insulates the gate electrode from the balance of the OTFT device. Useful materials for the gate dielectric can comprise, for example, an inorganic electrically insulating material.

Specific examples of materials useful for the gate dielectric include strontiates, tantalates, titanates, zirconates, aluminum oxides, silicon oxides, tantalum oxides, titanium oxides, silicon nitrides, barium titanate, barium strontium titanate, barium zirconate titanate, zinc selenide, and zinc sulfide. In addition, alloys, combinations, and multilayers of these materials can be used for the gate dielectric.

The source electrode and drain electrode are separated from the gate electrode by the gate dielectric, while the organic semiconductor layer can be over or under the source electrode and drain electrode. The source and drain electrodes can be any useful conductive material. Useful materials include most of those materials described above for the gate electrode, for example, aluminum, barium, calcium, chromium, gold, silver, nickel, palladium, platinum, titanium, polyaniline, PEDOT:PSS, other conducting polymers, alloys thereof, combinations thereof, and multilayers thereof. Some of these materials are appropriate for use with n-type semiconductor materials and others are appropriate for use with p-type semiconductor materials, as is known in the art.

The thin film electrodes (that is, the gate electrode, the source electrode, and the drain electrode) can be provided by any useful means such as physical vapor deposition (for example, thermal evaporation or sputtering) or ink jet printing. The patterning of these electrodes can be accomplished by known methods such as shadow masking, additive photolithography, subtractive photolithography, printing, microcontact printing, and pattern coating.

The present invention further provides a thin film transistor device comprising a plurality of electrically conducting gate electrodes disposed on a substrate;

a gate insulator layer disposed on said electrically conducting gate electrodes;

an organic semiconductor layer disposed on said insulator layer substantially overlapping said gate electrodes; and a plurality of sets of electrically conductive source and drain electrodes disposed on said organic semiconductor layer such that each of said sets is in alignment with each of said gate electrodes;

wherein said organic semiconductor layer is an azaperylene compound of the formula I.

The present invention further provides a process for preparing a thin film transistor device comprising the steps of:

depositing a plurality of electrically conducting gate electrodes on a substrate;

depositing a gate insulator layer on said electrically conducting gate electrodes;

depositing a layer of an azaperylene compound of the formula I or a precursor thereof of formula II on said insulator layer such that said layer of compound of formula I or precursor of formula II substantially overlaps said gate electrodes;

depositing a plurality of sets of electrically conductive source and drain electrodes on said layer such that each of said sets is in alignment with each of said gate electrodes; and, in case that a precursor of formula II has been used, heating to convert said precursor to an azaperylene compound of the formula I, thereby producing the thin film transistor device.

Any suitable substrate can be used to prepare the thin films of the azaperylene compounds of the present invention as well as the thin films of the precursor thereof. Preferably, the substrate used to prepare the above thin films is a metal, silicon, plastic, paper, coated paper, fabric, glass or coated glass.

Alternatively, a TFT is fabricated by, for example, by solution deposition of an azaperylene or its precursor on a highly doped silicon substrate covered with a thermally grown oxide layer followed by vacuum deposition and patterning of source and drain electrodes. In the last step, the device is optionally heated so that the precursor is converted to an azaperylene film.

In yet another approach, a TFT is fabricated by deposition of source and drain electrodes on a highly doped silicon substrate covered with a thermally grown oxide and then solution deposition of the azaperylene or its precursor to form a thin film, and finally heating the device in case that the precursor has been used to convert it to azaperylene.

The gate electrode could also be a patterned metal gate electrode on a substrate or a conducting material such as, a conducting polymer, which is then coated with an insulator applied either by solution coating or by vacuum deposition on the patterned gate electrodes. The insulator can be a material, such as, an oxide, nitride, or it can be a material selected from the family of ferroelectric insulators, including but not limited to $PbZr_xT_{1-x}O_3$ (PZT), $Bi_4Ti_3O_{12}$, $BaMgF_4$, $Ba(Zr_{1-x}Ti_x)O_3$ (BZT), or it can be an organic polymeric insulator.

Any suitable solvent can be used to dissolve the precursor or the present azaperylene compound, provided it is inert, can dissolve at least some of material and can be removed from the substrate by conventional drying means (e.g. application of heat, reduced pressure, airflow etc.). Suitable organic solvent for processing the semiconductors of the invention include, but are not limited to, aromatic or aliphatic hydrocarbons, halogenated such as chlorinated hydrocarbons, esters, ethers amides, such as chloroform, tetrachloroethane, tetrahydrofuran, toluene, ethyl acetate, methyl ethyl ketone, dimethyl formamide, dichlorobenzene, propylene glycol monomethyl ether acetate (PGMEA) and mixtures thereof. The solution is then applied by a method, such as, spin-coating, dip-coating, screen printing, microcontact printing, doctor blading or other solution application techniques known in the art on the substrate to obtain thin films of the semicunducting material or its precursor.

Preferably, the thickness of the organic semiconductor layer is in the range of from about 5 to about 200 nm, especially the thickness is in the range of from about 10 to about 30 nm.

The azaperylene compounds of the invention can be used alone or in combination as the organic semiconductor layer of the semiconductor device. The layer can be provided by any useful means, such as, for example, vapor deposition and printing techniques. Some of the compounds of the invention (for example, those bearing sufficiently large alkyl groups such as two dodecyl, nonyl, or hexyl substituents, especially unbranched ones which are uninterrupted, or branched or unbranched interrupted groups such as alkyls branched in α-position to the heterofunction) are sufficiently soluble in organic solvents and can be solution deposited (for example, by spin coating, dip coating, ink jet printing, casting, or other known techniques).

In case of chiral side chains, the selection of diastereomerically pure molecules for the preparation of the semiconducting layer is preferred.

The azaperylene compounds of the invention can be used in integrated circuits comprising a plurality of OTFTs, as well as in various electronic articles. Such articles include, for example, radio-frequency identification (RFID) tags, backplanes for flexible displays (for use in, for example, personal computers, cell phones, or handheld devices), smart cards, memory devices, and the like.

The following examples are for illustrative purposes only and are not to be construed to limit the instant invention in any manner whatsoever. Room temperature depicts a temperature in the range 20-25° C. Percentages are by weight unless otherwise indicated.

Abbreviations used in the examples or elsewhere:
M concentration in moles per litre

PREPARATION EXAMPLES

Example 1

Compound 605 is prepared according to K. Kitahara, H. Nishi, J. Heterocycl. Chem. 1988, 25, 1063.

605

Example 2

487 mg of compound No. 605 of example 1 and 72 mg of sodium hydride are stirred at room temperature for 2 hours under nitrogen in 10 ml of N-methylpyrrolidon. Subsequently, 771 mg of 1-bromdodecane are added; stirring is continued for 18 hours at room temperature and then for 24 hours at 70° C. After cooling to room temperature, 20 ml of water and 50 ml of $CHCl_3$ are added while stirring is continued for further 10 min. The organic phase is separated, dried over sodium sulphate, filtered, and the solvent is removed under reduced pressure. The residue is subjected to chromatography on silica, and the product obtained is recrystallized from hot ethanol, yielding 396 mg of a yellow solid (compound No. 653) of the formula

653

1H-NMR (CHCl$_3$): 9.14-9.08 (m, 2H); 8.96 (d, 2H); 8.83-8.77 (m, 2H); 8.40 (dd, 2H); 7.84-7.76 (m, 6H); 7.73-7.66 (m, 2H); 4.30 (t, 4H); 2.18-2.02 (m, 4H); 1.70-1.55 (m, 4H); 1.47-1.20 (m, 32H); 0.90 (t, 6H).

$^{13}$C-NMR (CHCl$_3$): 155.4 (2C); 149.0 (2C); 145.8 (2C); 132.1 (2C); 130.5 (2C); 129.9 (2C); 128.3 (2C); 128.1 (2C); 128.0 (2C); 127.9 (2C); 127.8 (2C); 126.9 (2C); 126.5 (2C); 124.5 (2C); 123.0 (2C); 122.9 (2C); 117.5 (2C); 75.0 (2C); 32.0 (2C); 30.6 (2C); 29.7 (10C); 29.5 (2C); 26.5 (2C); 22.8 (2C); 14.2 (2C).

IR (cm$^{-1}$): 3060, 2917, 2849, 1580, 1570, 1488, 1470, 1449, 1430, 1397, 1371, 1321, 1298, 1225, 1207, 1188, 1147, 1109, 1077, 1036, 1018, 945, 756, 718.

Figure 1:
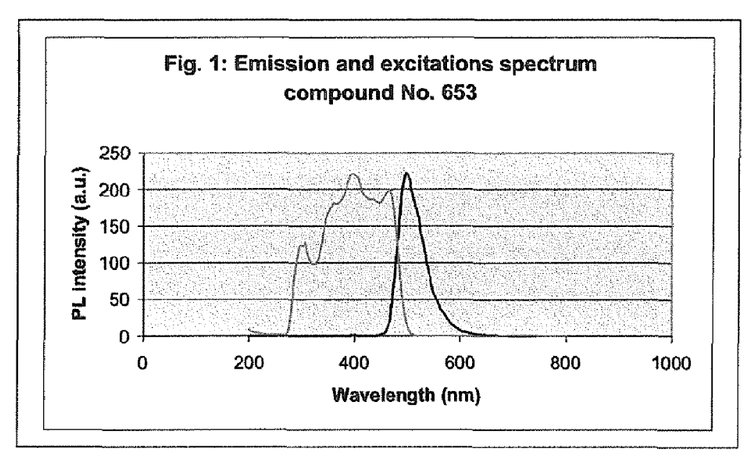
FIG. 1 represents the emission and excitations spectrum of compound No. 653.

Photophysical properties: The spectra of 10$^{-04}$ M solutions in toluene are recorded on a Perkin Elmer (LS-50B) fluorescence spectrometer, showing a peak emission at 498 nm. FIG. 1 shows the emission and excitation spectrum of compound 653.

In the solid film, the fluorescence intensity is surpressed showing an orange emission. The absorption spectrum shows a maximum at 325 nm and more resolved bands in the 420-450 nm region.

Example 3

A mixture of 2.51 g dimethyl-1,4-cyclohexanedione-2,5-dicarboxylate and 5.48 g 2-aminophenyl-2-thienylketone in 80 ml ethanol and 1 ml 6N hydrochloric acid is refluxed under a nitrogen atmosphere for 4 hours. After cooling, the precipitate is filtered off, washed with ethanol and dried in vacuum, yielding 4.1 g colorless crystals of compound No. 659 of the formula $^1$H-NMR (CHCl$_3$): 8.15 (d, 2H); 7.75-7.6 (m, 4H); 7.57 (d, 2H); 7.50-7.43 (m, 2H); 7.26-7.21 (m, 2H); 7.15 (br s, 2H); 5.59 (s, 2H); 3.64 (s, 6H).

$^{13}$C-NMR (CDCl$_3$): 169.6 (2C); 153.7 (2C); 147.1 (2C); 141.5 (2C); 134.4 (2C); 129.7 (2C); 129.4 (2C); 129.0 (2C); 128.0 (2C); 127.6 (2C); 127.5 (2C); 127.0 (2C); 126.5 (2C); 126.2 (2C); 54.2 (2C); 53.0 (2C).

Example 4

2.3 g of the compound synthesised in example 3 is heated under vacuum (0.1 mbar) to 350° C. for 2 hours. After cooling, 25 ml of dichloromethane are added and the suspension is filtered. The crude product is suspended in 80 ml of nitrobenzene, heated to reflux for 5 minutes, cooled to room temperature and standing over night. The suspension is filtered, the crystallized product is washed with toluene and dichloromethane and dried at 80° C./25 mbar for 16 hours, yielding 1.3 g of dark violett crystals of compound No. 660 of the formula

APPLICATION EXAMPLES

A) Purification and Thin Film Preparation

Compound No. 605 is purified in a 3 zone-oven by train-sublimation using argon as a carrier gas. The purifed sample is charged in a vacuum vapour deposition apparatus (Balzers) and sublimed at a growth rate of 0.1 nm/s. Chamber pressure typically is 6×10$^{-6}$ Torr at the start and end of the deposition. The film thickness is measured by a quartz crystal monitor to give a total thickness of 50 nm.

B) Azapentacene-Based Field-Effect Transistors

Bottom-gate thin-film transistor (TFT) structures with p-Si gate (10 Ωcm) are used for all experiments. A high-quality thermal SiO$_2$ layer of 300 nm thickness serves as gate-insulator of $C_i$=11 nF/cm$^2$ capacitance per unit area. Source and drain electrodes are patterned by photolithography directly on the gate-oxide (bottom-contact configuration). Au source/drain electrodes defining channels of width W=2 mm and length L=50 μm are used. Prior to the deposition of the organic semiconductor, the SiO$_2$ surface is derivatized with hexamethyldisilazane (HMDS) by exposing it to saturated silane vapour at 160° C. for 2 hours.

Figure 2:
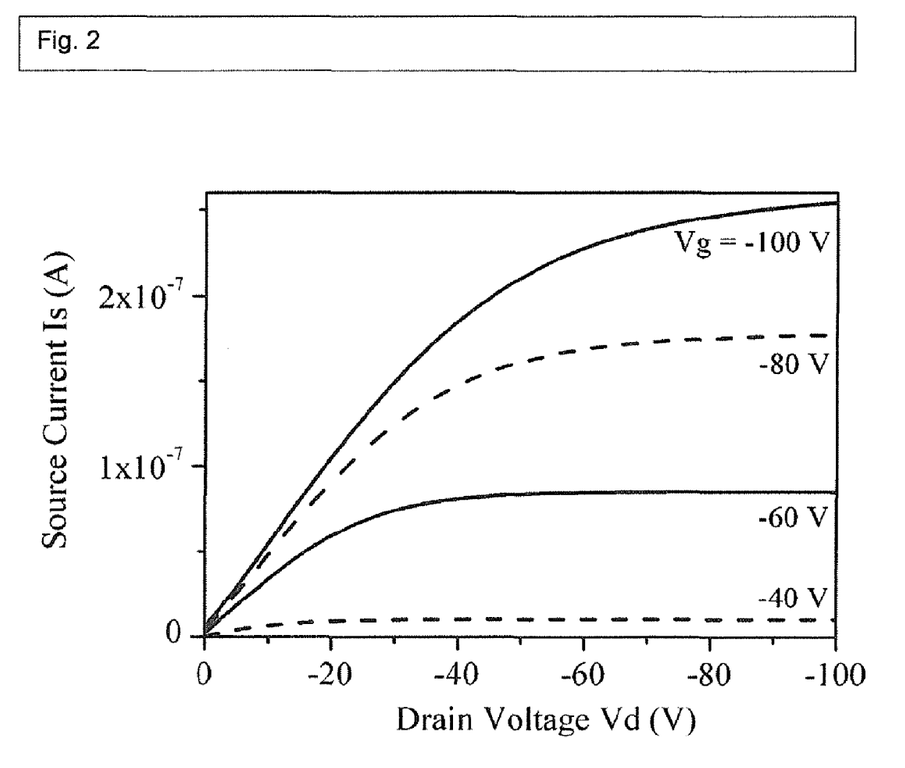
FIG. 2 is a graph of Source Current verses Drain voltage for an azapentacene thin-film transistor. This shows clear p-type transistor behavior.
Figure 3:
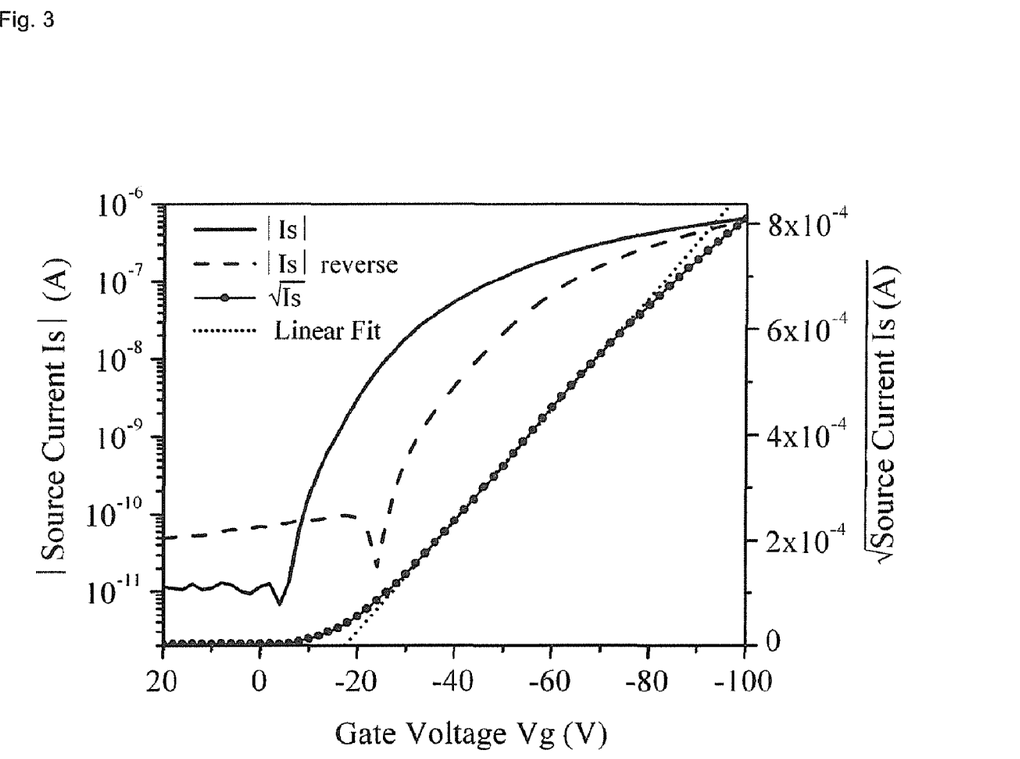
FIG. 3 is a graph of Source Current verses Gate Voltage. From a linear fit to the square root of the saturated transfer characteristics, a field-effect mobility of $5 \cdot 10^{-4}$ cm2/vs is determined.

Transistor Performance:

The azapentacene thin-film transistors show clear p-type transistor behavior (see FIG. 2). From a linear fit to the square root of the saturated transfer characteristics (see FIG. 3), a field-effect mobility of 5 10$^{-4}$ cm$^2$/Vs is determined (IEEE Standard 1620). With a 300 nm gate-oxide of 11 nF/cm$^2$ capacitance per unit area the transistors show a threshold voltage of about −20 V.

The transistors show good on/off current ratios of $10^4$ to $10^5$.

The invention claimed is:

1. A semiconductor device, or a device containing a semiconductor element, which semiconductor device or device containing a semiconductor element comprises an azaperylene organic semiconductor of the formula I (I)

wherein
each of R1, R2, R3 and R4 independently is selected from H, unsubstituted or substituted alkyl, unsubstituted or substituted alkenyl, unsubstituted or substituted alkynyl, unsubstituted or substituted aryl, halogen, substituted silyl, XR6; or one or more of R1 and R2, R2 and R3, R3 and R4, together with the carbon atoms they are bonding to, form a saturated or unsaturated, unsubstituted or substituted carbocyclic or heterocyclic ring;
R5 is OR7, SR7, NR7R8, unsubstituted or substituted alkyl, unsubstituted or substituted alkenyl, unsubstituted or substituted alkynyl, or unsubstituted or substituted aryl;
R6 is substituted silyl, unsubstituted or substituted alkyl, unsubstituted or substituted alkenyl, unsubstituted or substituted alkynyl, unsubstituted or substituted aryl;
R7 is H, unsubstituted or substituted alkyl, unsubstituted or substituted alkenyl, unsubstituted or substituted alkynyl, unsubstituted or substituted aryl;
X is O, S, NR8;
R8 is H, unsubstituted or substituted alkyl, unsubstituted or substituted alkenyl, unsubstituted or substituted alkynyl, unsubstituted or substituted aryl and
substituents, where present, bond to a carbon atom and are selected from the group consisting of $C_1$-$C_{22}$alkoxy, $C_1$-$C_{22}$alkyl, $C_4$-$C_{12}$cycloalkoxy, $C_4$-$C_{12}$cycloalkyl, OH, halogen, phenyl, and naphthyl; while saturated carbons also may be substituted by oxo (=O); 2 adjacent substituents may be linked together by abstraction of a hydrogen atom on each.

2. A semiconductor device according to claim 1, wherein in formula I each alkyl is selected from $C_1$-$C_{22}$alkyl, which may be interrupted by O, S, COO, OCNR10, OCOO, OCONR10, NR10CNR10, or NR10, where R10 is H, $C_1$-$C_{12}$alkyl, $C_4$-$C_{12}$cycloalkyl; each aryl is selected from $C_4$-$C_{18}$aromatic moieties, which may contain, as part of the ring structure, one or 2 heteroatoms selected from O, N and S.

3. A semiconductor device according to claim 1, where in the compounds of the formula I each of the adjacent residues R1 and R2, R3 and R4, together with the carbon atoms they are bonding to, form a saturated or unsaturated carbocyclic or N-heterocyclic 6-membered ring;
R5 is OR7, SR7; and
R7 is H, unsubstituted or substituted alkyl.

4. A semiconductor device according to claim 2, where the compound of the formula I is of the structure III (III)

wherein
R independently is H, halogen, OH, unsubstituted or substituted alkyl, unsubstituted or substituted alkoxy, unsubstituted or substituted alkylthio, unsubstituted or substituted aryl, and
R7 independently is H, alkyl, alkenyl or alkynyl.

5. A semiconductor device according to claim 1, wherein said device is selected from the group consisting of a diode, an organic field effect transistor, a device containing a diode and an organic field effect transistor.

6. A device according to claim 5, comprising a gate electrode, a gate dielectric on the gate electrode, a source electrode and a drain electrode adjacent to the gate dielectric, and a semiconductor layer adjacent to the gate dielectric and adjacent to the source and drain electrodes, wherein the semiconductor layer comprises a compound of the formula I or formula III (III)

wherein
R independently is H, halogen, OH, unsubstituted or substituted alkyl, unsubstituted or substituted alkoxy, unsubstituted or substituted alkylthio, unsubstituted or substituted aryl, and
R7 independently is H, alkyl, alkenyl or alkynyl.

7. A process for the preparation of an organic semiconductor device, which process comprises applying a solution of an azaperylene compound of the formula I according to claim 1, wherein at least one of R1-R7 contain an alkyl or alkyl of 4 or more carbon atoms;

in an organic solvent to a suitable substrate and removing the solvent.

8. A process for the preparation of an organic semiconductor device, which process comprises heating of an azaperylene precursor of the formula II' wherein

R1, R2, R3 and R4 are as defined for formula I in claim 1
X is O, and
R' is H, unsubstituted or substituted alkyl, unsubstituted or substituted aryl, to a temperature in the range 60-500° C.

9. A process according to claim 7 wherein the organic semiconductor devise is an organic thin film transistor, wherein a film of the azaperylene compound is formed having a thickness in the range of from 5 to 200 nm.

10. A compound of the formula I' wherein
each of R1, R2, R3 and R4 independently is selected from H, unsubstituted or substituted alkyl, unsubstituted or substituted alkenyl, unsubstituted or substituted alkynyl, unsubstituted or substituted aryl, halogen, Si(R11)$_3$, XR6; or one or more of R1 and R2, R2 and R3, R3 and R4, together with the carbon atoms they are bonding to, form a saturated or unsaturated, unsubstituted or substituted carbocyclic or heterocyclic ring;
R5 is H, OR7, SR7, NR7R8, unsubstituted or substituted alkyl, unsubstituted or substituted alkenyl, unsubstituted or substituted alkynyl, or unsubstituted or substituted aryl;
R6 is Si(R11)$_3$, unsubstituted or substituted alkyl, unsubstituted or substituted alkenyl, unsubstituted or substituted alkynyl, unsubstituted or substituted aryl;
R7 is H, unsubstituted or substituted alkyl, unsubstituted or substituted alkenyl, unsubstituted or substituted alkynyl, unsubstituted or substituted aryl;
X is O, S, NR8;
R8 is H, unsubstituted or substituted alkyl, unsubstituted or substituted alkenyl, unsubstituted or substituted alkynyl, unsubstituted or substituted aryl,
R11 being $C_1$-$C_{20}$-alkyl or alkoxy,
provided that at least one of R1, R2, R3, R4, R6, R7 is $C_4$-$C_{22}$alkyl, $C_{10}$-$C_{22}$phenylalkyl, or such residues interrupted by O, S, NR10, COO, OCNR10, OCOO, OCONR10, or NR10CNR10,
R10 is hydrogen, $C_1$-$C_{12}$alkyl, or $C_4$-$C_{12}$cycloalkyl,
and
substituents, where present, bond to a carbon atom and are selected from the group consisting of $C_1$-$C_{22}$alkoxy, $C_1$-$C_{22}$alkyl, $C_4$-$C_{12}$cycloalkoxy, $C_4$-$C_{12}$cycloalkyl, OH, halogen, phenyl, and naphthyl; while saturated carbons also may be substituted by oxo (=O); 2 adjacent substituents may be linked together by abstraction of a hydrogen atom on each.

11. A compound according to claim 10, wherein said compound is of the formula III, wherein each R independently is selected from H, halogen, OH, unsubstituted or substituted alkyl, unsubstituted or substituted alkoxy, unsubstituted or substituted alkylthio, unsubstituted or substituted aryl;
each R7 independently is selected from H, alkyl, alkenyl or alkynyl, and at least one of R, R$_7$ is $C_4$-$C_{22}$alkyl, $C_{10}$-$C_{22}$phenylalkyl, $C_4$-$C_{22}$alkyl interrupted by O, S, NR10, COO, OCNR10, OCOO, OCONR10, or NR10ONR10, or $C_{10}$-$C_{22}$phenylalkyl interrupted in the aliphatic part by O, S, NR10, COO, OCNR10, OCOO, OCONR10, or NR10CNR10.

12. A compound according to claim 10, wherein
each alkyl is selected from $C_1$-$C_{22}$alkyl, which may be interrupted by O, S, COO, OCNR10, OCOO, OCONR10, NR10CNR10, or NR10, where R10 is H, $C_1$-$C_{12}$alkyl, or $C_4$-$C_{12}$cycloalkyl; each aryl is selected from $C_4$-$C_{18}$aromatic moieties, which may contain, as part of the ring structure, one or 2 heteroatoms selected from O, N and S;
any substituent, where present, bond to a carbon atom and is selected from $C_1$-$C_{22}$alkoxy, $C_1$-$C_{22}$alkyl, $C_4$-$C_{12}$cycloalkoxy, $C_4$-$C_{12}$cycloalkyl, OH, halogen, phenyl, or naphthyl; while saturated carbons also may be substituted by oxo (=O); 2 adjacent substituents may be linked together to form a lactone, anhydride or imide ring.

13. A method for the manufacture of an organic semiconductor for the preparation or operation of an electronic device comprising applying to a substrate an effective electrically conducting amount of a compound of formula (I) according to claim 1 or structure (III)

(III)

wherein
R independently is H, halogen, OH, unsubstituted or substituted alkyl, unsubstituted or substituted alkoxy, unsubstituted or substituted alkylthio, unsubstituted or substituted aryl, and
R7 independently is H, alkyl, alkenyl or alkynyl.

14. A semiconductor device according to claim 2, wherein aryl is selected from the group consisting of phenyl, naphthyl, pyridyl, tetrahydronaphthyl, furyl, thienyl, pyrryl, chinolyl, isochinolyl, anthrachinyl, anthracyl, phenanthryl, pyrenyl, benzothiazolyl, benzoisothiazolyl, and benzothienyl.

15. A semiconductor device according to claim 4, wherein the compound of the formula I is structure III (III)

wherein
R independently is H, halogen, OH, unsubstituted or substituted alkyl, unsubstituted or substituted alkoxy, unsubstituted or substituted alkylthio, unsubstituted or substituted aryl, and
R7 independently is alkyl.

16. A semiconductor device according to claim 15, wherein the compound of the formula I is structure III

(III)

wherein
at least one of R and $R_7$ is independently $C_4$-$C_{22}$alkyl; $C_{10}$-$C_{22}$phenylalkyl; $C_4$-$C_{22}$alkyl interrupted by O, S, NR10, COO, OCNR10, OCOO, OCONR10, or NR10CNR10; or $C_{10}$-$C_{22}$phenylalkyl interrupted in the aliphatic part by O, S, NR10, COO, OCNR10, OCOO, OCONR10, or NR10ONR10, and R10 is hydrogen, $C_1$-$C_{12}$alkyl, or $C_4$-$C_{12}$cycloalkyl.

17. A process for the preparation of an organic semiconductor device, which process comprises applying a solution of an azaperylene compound of the formula I according to claim 7, wherein 1 or 2 of R1-R7 contain a residue selected from the group consisting of $C_4$-$C_{22}$alkyl, $C_{10}$-$C_{22}$phenylalkyl, $C_4$-$C_{22}$alkyl interrupted by O, S, NR10, COO, OCNR10, OCOO, OCONR10, or NR10CNR10; and $C_{10}$-$C_{22}$phenylalkyl interrupted in the aliphatic part by O, S, NR10, COO, OCNR10, OCOO, OCONR10, or NR10ONR10;
in an organic solvent to a suitable substrate and removing the solvent wherein, R10 is hydrogen, $C_1$-$C_{12}$alkyl, or $C_4$-$C_{12}$cycloalkyl.

18. A compound according to claim 12, wherein aryl is selected from the group consisting of phenyl, naphthyl, pyridyl, tetrahydronaphthyl, furyl, thienyl, pyrryl, chinolyl, isochinolyl, anthrachinyl, anthracyl, phenanthryl, pyrenyl, benzothiazolyl, benzoisothiazolyl, and benzothienyl.

19. A method for the manufacture of an organic semiconductor for the preparation or operation of an electronic device comprising applying to a substrate an effective electrically conducting amount of a compound of formula (I') according to claim 10 or formula (III)

(III)

wherein
R independently is H, halogen, OH, unsubstituted or substituted alkyl, unsubstituted or substituted alkoxy, unsubstituted or substituted alkylthio, unsubstituted or substituted aryl, and
R7 independently is H, alkyl, alkenyl or alkynyl.

* * * * *